United States Patent [19]

Clark et al.

[11] Patent Number: 4,609,394
[45] Date of Patent: Sep. 2, 1986

[54] PHENYL BENZOTHIADIAZOLE ETHER HERBICIDES

[75] Inventors: Michael T. Clark, Sittingbourne; David Munro, Maidstone; Ian J. Gilmore, Sittingbourne, all of England

[73] Assignee: Shell Oil Company, Houston, Tex.

[21] Appl. No.: 789,296

[22] Filed: Oct. 18, 1985

[30] Foreign Application Priority Data

Oct. 18, 1984 [GB] United Kingdom ................. 8426367

[51] Int. Cl.$^4$ .................... C07D 285/06; A01N 43/82
[52] U.S. Cl. .......................................... 71/90; 548/127
[58] Field of Search ............................. 548/127; 71/90

[56] References Cited

U.S. PATENT DOCUMENTS 4,556,411 12/1985 Baum ....................................... 71/90

Primary Examiner—Robert Gerstl

[57] ABSTRACT

Compounds of the formula

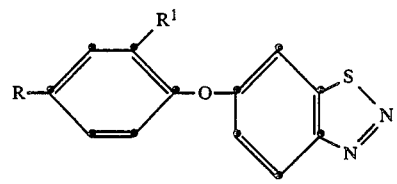

wherein the symbols have assigned meanings, and their use as herbicides.

6 Claims, No Drawings

PHENYL BENZOTHIADIAZOLE ETHER HERBICIDES

DESCRIPTION OF THE INVENTION

It has been found that useful herbicidal properties are possessed by compounds of the formula:

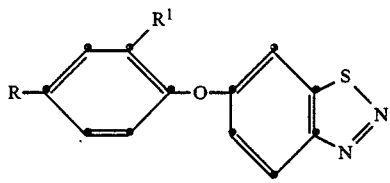

wherein R is halogen or haloalkyl of one to six carbon atoms and $R^1$ is hydrogen, halogen, nitro, cyano or haloalkyl of one to six carbon atoms.

Preferably, the halogen represented by R and $R^1$ is chlorine, any haloalkyl moiety contains from one to four carbon atoms and the halogen atom(s) is or are fluorine or chlorine, trifluoromethyl being the most preferred haloalkyl moiety.

Compounds of Formula I can be prepared by cyclizing a compound of the formula:

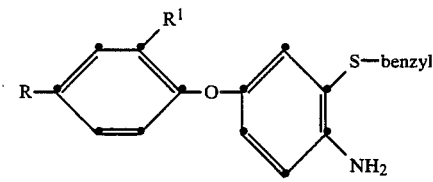

The cyclization is suitably effected by treating the compound of Formula II with an aqueous solution of an alkali metal nitrite, conveniently sodium nitrite, in the presence of an acid, conveniently a mineral acid such as sulfuric acid, at a temperature not exceeding 10° C.

Compounds of Formula II can be prepared by treating a compound of the formula:

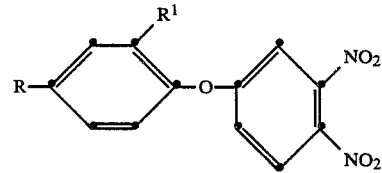

with benzyl mercaptan, in a polar organic solvent such as tetrahydrofuran, to give the product of the formula

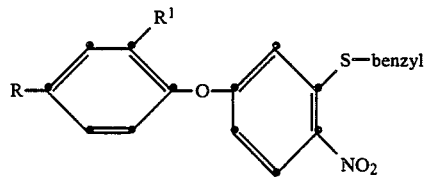

which then is treated with sodium dihydrogen phosphite ($NaH_2PO_2$) in the presence of a palladium/carbon catalyst to give the compound of Formula II.

Compounds of Formula I have been found to show interesting activity as herbicides.

For application, a compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides—i.e., horticulturally acceptable carriers—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.05 to 4.0 kilograms per hectare of the compound of Formula I will be satisfactory.

The invention is illustrated in the following examples.

EXAMPLE 1

6-(2-Chloro-4-trifluoromethylphenoxy)-1,2,3-benzothiadiazole (1)

(A) 30.6 g of m-nitrophenol was dissolved in 100 ml of dimethylsulfoxide, and 14.5 g of potassium hydroxide added with stirring under nitrogen at 80° C. After 1.5 hours, 43 g of 3,4-dichlorobenzotrifluoride was added drop by drop over 30 minutes and the temperature increased to 150° C. followed by stirring overnight. The bulk of the dimethylsulfoxide was removed, 1 liter of a 1:1 v:v mixture of ether and water added, the suspension filtered, and the organic layer separated, dried and evaporated to yield an orange oil, which was chromatographically purified. This oil (35 g) was dissolved in 70 ml of ethylene dichloride, and concentrated sulfuric acid was added with stirring and cooling. When the reaction mixture was below 2° C., 11.6 g of potassium nitrate was added in portions over 30 minutes. The reaction mixture was then allowed to warm to ambient temperature, stirred for 3 hours, and then poured into 1 liter of ice water followed by addition of sodium chloride and extraction with ethylene dichloride. The organic layers were separated, dried, solvent removed, chromatographically purified and the product recrystallized to yield 4-(2-chloro-4-trifluoromethylphenoxy)-1,2-dinitrobenzene (1A), as a solid, m.p.: 80°–81° C.

(B) 1.7 g of benzyl mercaptan was dissolved in dry tetrahydrofuran and 0.5 g of sodium hydride added with stirring under dry nitrogen. The reaction mixture was stirred under reflux for 30 minutes, and a solution of 5 g of 1A dissolved in 25 ml of dry tetrahydrofuran was added dropwise. Reaction occurred rapidly, and the product was chromatographically purified to give 2-benzylthio-4-(2-chloro-4-trifluoromethylphenoxy)nitrobenzene (1B) as a yellow oil.

(C) 2 g of 1B was dissolved in 30 ml of ethanol and 0.5 g of 5% palladium on carbon catalyst and 10% aqueous sodium dihydrogen phosphite added in portions until vigorous effervescence ceased. The reaction mixture was filtered, extracted with 400 ml of a 1:1 v:v mixture of ethylene dichloride/water, and the organic layer separated and dried. Chromatographic purification yielded 2-benzylthio-4-(2-chloro-4-trifluoromethylphenoxy)aniline (1C) as a brown oil.

(D) 3 g of 1C was added to an ice-cold solution of 50% aqueous sulfuric acid, and the mixture maintained below 10° C. during the addition of a solution of 0.7 g of sodium nitrite in 10 ml of water. This mixture was then stirred for 1 hour, allowed to reach ambient temperature, and then extracted with ether. The organic layer was separated, solvent removed and the resulting red oil chromatographically purified and recrystallized to yield 1, as a crystalline solid, m.p.: 72°–73° C.

Analysis: Calculated for $C_{13}H_6N_2ClF_3OS$: C 47.2; H 1.8; N 8.5%; Found: C 47.1; H 1.7; N 8.2%.

EXAMPLE 2

Following synthetic procedures similar to those of Example 1, there was prepared 6-(2-nitro-4-trifluoromethylphenoxy)-1,2,3-benzothiazole, as a solid, m.p.: 97°–99° C.

Herbicidal Activity

To evaluate their herbicidal activity, compounds according to the invention were tested using as representative range of plants: maize, Zea mays (Mz); rice, Oryza sativa (R); barnyard grass, Echinochloa crusgalli (BG); oat, Avena sativa (O); linseed, Linum usitatissimum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 20% increase in the level of effect.

The results of the tests are set out in Table 1 below, in which the compounds are identified by reference to the preceding examples.

TABLE 1

| Compound of Example No. | Soil Drench (10 kg/ha) | | | | | | | | Dosage (kg/ha) | Foliar Spray | | | | | | | | Pre-Emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | 5 | 5 | 4 | 7 | 6 | 2 | 7 | 2 | 5 | 8 | 6 | 9 | 9 | 9 | 9 | 9 | 9 | 7 | 7 | 9 | 7 | 6 | 6 | 9 | 0 |
| | | | | | | | | | 1 | 7 | 4 | 9 | 8 | 9 | 8 | 9 | 8 | 6 | 6 | 9 | 6 | 5 | 4 | 8 | 0 |
| 2 | 0 | 0 | 0 | 0 | 0 | 0 | 0 | 0 | 5 | 7 | 5 | 8 | 5 | 6 | 9 | 9 | 7 | 0 | 3 | 5 | 0 | 0 | 4 | 8 | 2 |
| | | | | | | | | | 1 | 5 | 4 | 5 | 4 | 5 | 8 | 7 | 4 | 0 | 2 | 4 | 0 | 0 | 2 | 6 | 0 |

We claim:

1. A compound of the formula:

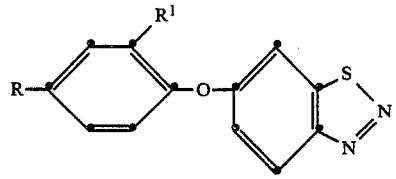

wherein R is halogen or haloalkyl of one to six carbon atoms and $R^1$ is hydrogen, halogen, nitro, cyano or haloalkyl of one to six carbon atoms.

2. The compound according to claim 1 wherein R is trifluoromethyl and $R^1$ is chlorine.

3. A herbicidal composition comprising an effective amount of a compound of claim 1 together with a carrier and a surface-active agent.

4. A herbicidal composition comprising an effective amount of a compound of claim 2 together with a carrier and a surface-active agent.

5. A method of combatting undesired plant growth at a locus, that comprises treating the locus with an effective amount of a compound of claim 1.

6. A method of combatting undesired plant growth at a locus, that comprises treating the locus with an effective amount of a compound of claim 2.

* * * * *